United States Patent [19]

Pepperman, Jr. et al.

[11] 4,102,923

[45] Jul. 25, 1978

[54] TRIS(UREIDOMETHYL)PHOSPHINE OXIDES

[75] Inventors: Armand B. Pepperman, Jr., Metairie; Donald J. Daigle, New Orleans; Sidney L. Vail, River Ridge, all of La.

[73] Assignee: The United States of America as represented by the Secretary of Agriculture, Washington, D.C.

[21] Appl. No.: 611,460

[22] Filed: Sep. 8, 1975

[51] Int. Cl.$^2$ .................................. C07C 127/00
[52] U.S. Cl. ........................... 260/553 R; 260/553 A; 427/382; 427/390 D; 428/920; 428/921
[58] Field of Search ............ 428/DIG. 921, 920; 427/382, 390 D; 260/553 R, 553 A, 938, DIG. 24

[56]  References Cited
U.S. PATENT DOCUMENTS

| 2,809,941 | 10/1957 | Reeves et al. | 427/390 D |
| 2,814,573 | 11/1957 | Reeves | 260/606.5 P |
| 2,861,901 | 11/1958 | Reeves et al. | 427/390 D |
| 3,268,360 | 8/1966 | Beninate et al. | 427/390 D |
| 3,376,160 | 4/1968 | LeBlanc | 427/390 D |
| 3,619,113 | 9/1971 | Stockel et al. | 427/390 D |
| 3,765,837 | 10/1973 | Aycock et a. | 427/390 D |

Primary Examiner—Ronald H. Smith
Assistant Examiner—Janyce A. Bell
Attorney, Agent, or Firm—M. Howard Silverstein; Salvador J. Cangemi; David G. McConnell

[57] ABSTRACT

Tris(4-substitutedureidomethyl)phosphine oxides were prepared by the reaction of tris(hydroxymethyl)phosphine with substituted ureas. The phosphine oxides were used to impart flame retardancy to cellulosic materials. They were effective as flame retardants either alone or in combination with hydroxymethylphosphorus compounds or hydroxymethylnitrogen compounds.

6 Claims, No Drawings

TRIS(UREIDOMETHYL)PHOSPHINE OXIDES

This invention relates to tris(ureidomethyl)phosphine oxides which are useful as flame retardants for cellulosic textiles and to methods of their preparation. In particular, this invention discloses tris(4-methylureidomethyl)phosphine oxide, tris(4-ethylureidomethyl)phosphine oxide, tris(4-dodecylureidomethyl)phosphine oxide, tris(4-t-butylureidomethyl)phosphine oxide, tris(4-phenylureidomethyl)phosphine oxide, and tris(4,4-diphenylureidomethyl)phosphine oxide.

The main object of the instant invention is to provide new phosphine oxides containing a substituted urea group attached to the phosphorus atom by a methylene (—CH$_2$—) linkage.

A second object of the instant invention is to provide methods of preparing new phosphine oxides.

A third object of the instant invention is to provide a process for imparting to cotton and other cellulosic materials flame resistance.

Searching the prior art we find that aminomethyl phosphines can be prepared by reacting a secondary amine with tris(hydroxymethyl)phosphine by itself or in the presence of formaldehyde [K. A. Petrov, V. A. Parshina, B. A. Orlov, and G. M. Tsypina, Zhur. Obshch. Khim., 32, 4017 (1962); D. J. Daigle, A. B. Pepperman, and W. A. Reeves, Text. Res. J., 41, 944 (1971)]. Urea itself reacts with tris(hydroxymethyl)phosphine to give polymeric materials in a similar reaction [W. A. Reeves and J. D. Guthrie, Ind. Eng. Chem., 48, 64 (1956)]. Monomeric products are obtained when trialkyl phosphites are permitted to react with substituted ureas in the presence of formaldehyde [G. H. Birum, J. Org. Chem., 39, 209 (1974)]. The present invention differs from those of the prior art in that substituted ureas are reacting with tris(hydroxymethyl)phosphine to give tris(4-substituted-ureidomethyl)phosphine oxides. Thus, a trifunctional urea derivative of tris(hydroxymethyl)phosphine has been prepared for the first time.

In the course of the investigation we have found that compounds of the general formula, $$(R_1R_2NCONHCH_2)_3P = O \quad (A)$$

where $R_1$ is methyl, ethyl, dodecyl, t-butyl, or phenyl and $R_2$ is hydrogen or where $R_1 = R_2$ is phenyl, can be prepared by reacting substituted ureas with tris(hydroxymethyl)phosphine.

In accordance with the present invention, the reaction of tris(hydroxymethyl)phosphine with substituted ureas is carried out by mixing the reagents in an appropriate solvent at reflux temperature of the solvent while removing the water formed in the reaction from the distillate. The solvent may be a polar solvent such as ethanol, in which case the water is removed by percolation of the distillate through Linde molecular sieve 4A; or the solvent may be a nonpolar solvent such as toluene, in which case the water is removed by separation of the water from the distillate by use of a Dean-Stark trap. Both types of solvents and water removal systems were effective. Reaction times were shorter for higher boiling solvents such as toluene.

The phosphine oxides are useful as flame retardants for cellulosic materials. Cotton fabric was made flame retardant by impregnating the fabric with a 23.5 weight % aqueous solution of equal weights of tris(4-methylureidomethyl)phosphine oxide and trimethylol melamine, drying the fabric at 85° C for 2 minutes and curing at 150° C for 2 minutes. Using a similar drying and curing procedure, a 25.8 weight % ethanolic solution of tris(4-t-butylureidomethyl)phosphine oxide flameproofed cotton fabric, rayon fabric and paper. An equal weight mixture of tris(4-ethylureidomethyl)phosphine oxide and tris(hydroxymethyl)phosphine (22.4 weight % total) was padded onto cotton fabric, dried at 85° C for 2 minutes and cured for 2 minutes at 150° or 160° C to yield a flameproofed cotton fabric. The concentration of the phosphine oxides may be varied as well as the curing times and temperatures.

The following examples illustrate the methods of carrying out the invention and are included for purposes of illustration, not as a limitation thereof. All percentages given as weight percentages.

Preparation of Tris(ureidomethyl)phosphine Oxides

Method a consisted of mixing tris(hydroxymethyl)phosphine (0.015–0.1 mol) with the substituted urea (0.045–0.3 mol) in a 1:3 molar ratio in sufficient ethanol (75–200 ml) to produce a 16–20% weight concentration of reactants. The mixture was heated to reflux and the water formed in the condensation was removed by drying the distillate in a Soxhlet tube containing a corundum thimble filled with Linde molecular sieve 4A. Reaction was allowed to proceed for one week or until a large amount of precipitate had formed in the reaction flask. Workup varied depending on the original urea.

Method b consisted of mixing tris(hydroxymethyl)phosphine (0.004–0.02 mol) with the substituted urea (0.012–0.06 mol) in a 1:3 molar ratio in 50–75 ml of toluene. The heterogeneous mixture was heated to reflux and the water formed in the condensation was collected in a Dean-Stark trap. Reflux was allowed to proceed until water evolution ceased or until theoretical water was collected (<8 hrs). Solid precipitated from the reaction mixture on cooling and was recrystallized from an appropriate solvent. A summary of the yields, recrystallizing solvents, and mp's of the compounds are given in Table I.

Table I

Tris(4-substituted)Ureidomethyl Phosphine Oxides
$(R_1R_2NCONHCH_2)_3P = O$

| Compound No. | $R_1$ | $R_2$ | Method | Crude Yield, % | Recrystallizing Solvent | MP, °C |
|---|---|---|---|---|---|---|
| 1 | CH$_3$ | H | a | 15 | ethanol | 233–34 |
| " | " | " | b | 54 | | |
| 2 | C$_2$H$_5$ | H | a | 14 | ethanol-ethyl acetate | 244 |
| " | " | " | b | 97 | | |
| 3 | CH$_3$(CH$_2$)$_{11}$ | H | a | 94 | ethanol-ethyl acetate | 170 |
| " | " | " | b | 67 | | |
| 4 | (CH$_3$)$_3$C | H | a | 61 | ethanol-water | 220 |
| " | " | " | b | 82 | | |
| 5 | C$_6$H$_5$ | H | a | 53 | dimethyl sulfoxide-water | 263–64 |
| " | " | " | b | 37 | | |

Table I-continued

Tris(4-substituted)Ureidomethyl Phosphine Oxides
$(R_1R_2NCONHCH_2)_3P = O$

| Compound No. | $R_1$ | $R_2$ | Method | Crude Yield, % | Recrystallizing Solvent | MP, °C |
|---|---|---|---|---|---|---|
| 6 | $C_6H_5$ | $C_6H_5$ | a | 38 | acetone | 147–48 |

EXAMPLE 1

Tris(4-methylureidomethyl)phosphine Oxide (1)

Method a afforded a 15% yield of white solid after a refluxing acetone trituration of the oil which resulted from removal of ethanol from the reaction mixture.

Method b gave a 54% yield after a similar workup. One recrystallization from ethanol gave the analytical sample, 1; ir (KBr) 3.02 μ (NH), 3.3–3.5 (aliphatic CH), 6.1 and 6.32 (amide bands), 8.68 (P = O); nmr (D$_2$O) δ 2.7 (s, 9H, CH$_3$), 3.77 (d, J = 4Hz, 6H, P-CH$_2$).

Anal. Calcd for $C_9H_{21}N_6O_4P$: C, 35.06; H 6.87; N, 27.26; P, 10.05. Found: C, 35.16; H, 6.96; N, 26.80; P, 9.91.

EXAMPLE 2

Tris(4-ethylureidomethyl)phosphine Oxide (2)

Method a gave a 14% yield of white solid after a refluxing acetone trituration of the oil which resulted from removal of ethanol from the reaction mixture.

Method b gave a 97% yield of white solid. One recrystallization from an acetone-ethanol mixture followed by a recristallization from ethanol afforded the analytical sample, 2; ir (KBr) 2.98 μ (NH), 3.31–3.4 (aliphatic CH), 6.08 and 6.38 (amide bands), 8.64 (P = O); nmr (D$_2$O) δ 1.1 (t, J = 7Hz, 9 H, CH$_3$CH$_2$), 3.2 (q, J = 7Hz, 6H, CH$_3$CH$_2$), 3.8 (d, J = 5Hz, 6 H, P-CH$_2$).

Anal. Calcd for $C_{12}H_{27}N_6O_4P$: C, 41.10; H, 7.77: N, 24.00; P, 8.84. Found: C, 41.24: H, 7.63; N, 24.18; P, 8.84.

EXAMPLE 3

Tris(4-dodecylureidomethyl)phosphine Oxide (3)

Method a yielded 94% of white solid.

Method b gave a 67% yield of solid. The product proved difficult to recrystallize as only powders would form from a variety of solvents and solvent pairs. The analytical sample, 3, was obtained after two recrystallizations from ethyl acetate-ethanol; ir (KBr) 2.99 μ (NH), 3.4 and 3.49 (aliphatic CH), 6.12 and 6.32 (amide bands) 8.7 (P = O).

Anal. Calcd for $C_{39}H_{81}N_6O_4P$: C, 64.25; H, 11.20; N, 11.53; P, 4.25. Found: C, 64.07; H, 10.97; N, 11.28; P, 4.10.

EXAMPLE 4

Tris(4-t-butylureidomethyl)phosphine Oxide (4)

Method a yielded 61% of white solid which precipitated after 3 days of reflux in ethanol.

Method b gave 82% of white solid. Recrystallization four times from ethanol-water gave a white crystalline solid which softened at 132°–138°, then resolidified and melted at 220°–222°. The elemental analysis of this solid indicated a dihydrate of (4).

After further recrystallization some of this solid was dried in a vacuum oven at 140° until it had softened and resolidified. The mp of the dried solid (4d) was 220° while the undried solid (4u) exhibited both a low and a high melting point. The ir spectra of the two solids were identical, while the nmr spectra of 4d showed four protons, from the water, at δ3.6 which 4u did not. After D$_2$O exchange the spectra were identical; ir (KBr) 2.96 μ (NH), 3.3–3.35 (aliphatic CH), 6.00 and 6.40 (amide bands), 8.6 (P = O); nmr (mixture of CDCl$_3$-DMSO-d$_6$) δ1.3 (s, 27H, (CH$_3$)$_3$C), 3.6(4u, m, 10H, P-CH$_2$, 2H$_2$O), 3.6 (4d, m, 6H, P-CH$_2$) 5.8 (broad s, 3H, NH), 6.4 (broad s, 3H, NH); after D$_2$O exchange δ1.3 (s, 27H, (CH$_3$)$_3$C); 3.65 (m, 6H, P-CH$_2$).

The elemental analyses of 4d and 4u clearly showed that 2 moles of water were lost on drying.

Anal. Calcd for $C_{18}H_{39}N_6O_4P$: C, 49.75; H, 9.05; N, 19.34; P, 7.13. Found for 4d: C, 49.71; H, 8.86; N, 19.17; P, 7.19.

Anal. Calcd for $C_{18}H_{39}N_6O_4P \cdot 2H_2O$: C, 45.94; H, 9.21; N, 17.86; P, 6.58. Found for 4u: C, 45.86; H, 9.12; N, 17.55; P, 6.57.

EXAMPLE 5

Tris(4-phenylureidomethyl)phosphine Oxide (5)

Method a gave a 53% yield of white solid after only 48 hours in refluxing ethanol.

Method b afforded a 37% yield of solid. Recrystallization from dimethyl sulfoxide-water gave the analytical sample, 5; ir (KBr) 2.99 μ (NH), 3.25 (aromatic CH), 3.4 (aliphatic CH), 6.03, 6.24, 6.5 and 6.7 (overlapping amide bands and aromatic C = C), 8.59 (P = O); nmr (d$_6$-DMSO, 80°) δ3.7 (d of d, $J_{P-CH}$ = $J_{N-CH}$ = 5Hz, 6H, PCH$_2$), 6.56 (t, J = 5Hz, 3H, CH$_2$-NH), 6.7–7.65 (m, 15H, aromatics), 8.81 (s, 3H, PhNH); after D$_2$O exchange, δ2.74 (d, $J_{PCH}$ = 5Hz, 6H, P-CH$_2$), 6.7–7.65 (m, 15H, aromatics).

Anal. Calcd for $C_{24}H_{27}N_6O_4P$: C, 58.29; H, 5.50; N, 17.00; P, 6.27. Found: C, 58.34; H, 5.60; N, 16.99; P, 6.28.

EXAMPLE 6

Tris(4,4-diphenylureidomethyl)phosphine Oxide (6)

Method a yielded 38% of white solid after 10 days reflux. However, the first solid collected from the reaction mixture on cooling to ambient temperature was recovered diphenylurea. Addition of water to the ethanolic reaction mixture was necessary to precipitate 6 which was recrystallized from acetone-ethanol, then ethyl acetate-ethanol to yield the analytical sample, 6; ir (KBr) 2.98 μ (NH), 3.24 (aromatic CH), 3.39 (aliphatic CH), 5.98 and 6.7(amide bands), 8.65 (P = O); nmr (CDCl$_3$) δ3.67 (m, 6H, PCH$_2$), 5.6 (m, 3H, NH), 7.23 (m, 3OH aromatics); after D$_2$O exchange δ3.73 (d, J = 5Hz, 6 H, PCH$_2$), 7.23 (m, 3OH, aromatics). The elemental analysis indicated a dihydrate.

Anal. Calcd for $C_{42}H_{39}N_6O_4P \cdot 2H_2O$: C, 66.48; H, 5.71; N, 11.08; P, 4.08. Found: C, 66.41; H, 5.61; N, 11.00; P, 4.17.

CELLULOSE TREATMENTS

EXAMPLE 7

An aqueous-ethanol solution (2:1) containing 11.75% of tris(4-methylureidomethyl)phosphine oxide, 11.75% trimethylolmelamine (23.5% total solids) and 1% lactic acid catalyst was applied to 8 oz. cotton sateen fabric by passing through squeeze rolls to an 80% wet pickup, drying at 85° C for 2 minutes and curing at 150° C for 2 minutes. The fabric had a 19.2% weight gain and contained 1.22% phosphorus and 6.51% nitrogen.

The flame resistance of the fabrics was measured by the match test angle. This test consists of cutting a small specimen (about 1 cm × 7 cm) of the fabric to be evaluated, placing the specimen above the flame of a kitchen match with the long axis of the fabric specimen at an angle of 180° to the flame, igniting the specimen, removing the flaming specimen from the flame and rotating the specimen until the flame is extinguished and recording that angle. The 0° angle (which untreated cotton would exhibit) would be where the flame is at the top of the specimen, and the most severe test would be where the flame would be at the bottom. This would be the 180° angle and would be exhibited only by very effective flame retardant materials. The cotton sateen treated in Example 7 had a match test angle of 135°.

EXAMPLE 8

Cotton sateen was treated with an aqueous-ethanol solution (2:1) containing 11.2% tris(4-ethylureidomethyl)phosphine oxide, 11.2% tris(hydroxymethyl)phosphine (22.4% total solids) and 1% lactic acid by padding through squeeze rolls to a 70% wet pickup, drying at 85° C for 2 minutes and curing at 150° C or 160° C for 2 minutes. The fabric cured at 150° C had a 14.5% add-on, contained 3.05% phosphorus, 1.44% nitrogen, and had a 180° match test angle. The fabric cured at 160° C had a 15.9% add-on, contained 3.18% phosphorus and 1.55% nitrogen, and had a 180° match test angle.

EXAMPLE 9

Cotton sateen, rayon challis, and filter paper were treated with an ethanolic solution containing 25.8% tris(4-t-butylureidomethyl)phosphine oxide and 1% lactic acid by padding through squeeze rolls, drying at 85° C for 2 minutes and curing at 150° C for 2 minutes. The cotton sateen had a 26.3% add-on, contained 1.42% phosphorus, 2.57% nitrogen and had a 90° match test angle. The rayon challis had a 28.7% add-on, contained 1.57% phosphorus, 2.36% nitrogen, and had a 90° match test angle. The filter paper had a 40.7% add-on, contained 2.19% phosphorus, 3.99% nitrogen, and had a 120° match test angle.

We claim:
1. Tris(4-methylureidomethyl)phosphine oxide.
2. Tris(4-ethylureidomethyl)phosphine oxide.
3. Tris(4-dodecylureidomethyl)phosphine oxide.
4. Tris(4-t-butylureidomethyl)phosphine oxide.
5. Tris(4-phenylureidomethyl)phosphine oxide.
6. Tris(4,4-diphenylureidomethyl)phosphine oxide.

* * * * *